United States Patent
Zhou et al.

(10) Patent No.: US 11,328,412 B2
(45) Date of Patent: May 10, 2022

(54) HIERARCHICAL LEARNING OF WEIGHTS OF A NEURAL NETWORK FOR PERFORMING MULTIPLE ANALYSES

(71) Applicant: Siemens Healthcare GmbH, Erlangen (DE)

(72) Inventors: Shaohua Kevin Zhou, Plainsboro, NJ (US); Mingqing Chen, Plainsboro, NJ (US); Daguang Xu, Princeton, NJ (US); Zhoubing Xu, Plainsboro, NJ (US); Shun Miao, Princeton, NJ (US); Dong Yang, Somerset, NJ (US); He Zhang, Edison, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 131 days.

(21) Appl. No.: 15/865,581

(22) Filed: Jan. 9, 2018

(65) Prior Publication Data
US 2018/0225822 A1    Aug. 9, 2018

Related U.S. Application Data

(60) Provisional application No. 62/456,368, filed on Feb. 8, 2017.

(51) Int. Cl.
*G06K 9/00* (2022.01)
*G06T 7/00* (2017.01)
(Continued)

(52) U.S. Cl.
CPC ......... *G06T 7/0012* (2013.01); *G06N 3/0454* (2013.01); *G06T 7/10* (2017.01);
(Continued)

(58) Field of Classification Search
CPC ........ G06N 3/0454; G06T 2207/20081; G06T 2207/20084; G06T 7/10; G06T 7/0012; Y04S 10/54
See application file for complete search history.

(56) References Cited

U.S. PATENT DOCUMENTS

| | | | |
|---|---|---|---|
| 6,018,728 A | 1/2000 | Spence et al. | |
| 6,035,057 A | 3/2000 | Hoffman | |

(Continued)

FOREIGN PATENT DOCUMENTS

| | | |
|---|---|---|
| CN | 105160397 A | 12/2015 |
| CN | 105469041 A | 4/2016 |
| CN | 106127217 A | 11/2016 |

OTHER PUBLICATIONS

Dai, Jifeng et al: "Instance-Aware Semantic Segmentation via Multi-task Network Cascades"; 2016 IEEE Conference on Computer Vision and Pattern Recognition (CVPR), IEEE, Jun. 27, 2016 (Jun. 27, 2016); pp. 3150-3158.

(Continued)

*Primary Examiner* — Xin Jia

(57) ABSTRACT

Systems and methods are provided for performing medical imaging analysis. Input medical imaging data is received for performing a particular one of a plurality of medical imaging analyses. An output that provides a result of the particular medical imaging analysis on the input medical imaging data is generated using a neural network trained to perform the plurality of medical imaging analyses. The neural network is trained by learning one or more weights associated with the particular medical imaging analysis using one or more weights associated with a different one of the plurality of medical imaging analyses. The generated output is outputted for performing the particular medical imaging analysis.

15 Claims, 7 Drawing Sheets

(51) Int. Cl.
*G06T 7/10* (2017.01)
*G06N 3/04* (2006.01)

(52) U.S. Cl.
CPC .............. *G06T 2207/20081* (2013.01); *G06T 2207/20084* (2013.01)

(56) References Cited

U.S. PATENT DOCUMENTS

| | | | |
|---|---|---|---|
| 6,324,532 | B1 | 11/2001 | Spence et al. |
| 7,545,965 | B2 | 6/2009 | Suzuki et al. |
| 8,775,341 | B1 | 7/2014 | Commons |
| 9,015,093 | B1* | 4/2015 | Commons .......... G01C 21/3602 706/26 |
| 9,633,306 | B2 | 4/2017 | Liu et al. |
| 9,760,807 | B2 | 9/2017 | Zhou et al. |
| 10,650,328 | B2 | 5/2020 | Vinyals et al. |
| 2015/0112182 | A1* | 4/2015 | Sharma ................ A61B 5/0261 600/408 |
| 2016/0328643 | A1* | 11/2016 | Liu ........................ G06N 3/084 |

OTHER PUBLICATIONS

Misra, Ishan et al.: "Cross-stitch Networks for Multi-task Learning"; 2016 IEEE Conference on Computer Vision and Pattern Recognition (CVPR); IEEE; Jun. 27, 2016 (Jun. 27, 2016); pp. 3994-4003.

Xu, Yan et al.: "Gland Instance Segmentation by Deep Multichannel Neural Networks"; arxiv. org; Cornell University Library, 201, Olin Library Cornell University Ithaca, NY 14853; Jul. 17, 2016.

Kisilev, Pavel et al.: "Medical Image Description Using Multi-task-loss CNN"; Medical Image Computing and Computer-Assisted Intervention—MICCAI 2015: 18th International Conference, Munich, Germany, Oct. 5-9, 2015; Proceedings; [Lecture Notes in Computer Science; Lect. Notes Computer]; Springer International Publishing, CH.

European Search Report dated Jul. 2, 2018 in corresponding European patent application No. 18154195.4.

Donahue et al., "DeCAF: A Deep Convolutional Activation Feature for Generic Visual Recognition", Proceedings of the 31st International Conference on Machine Learning, Beijing, China, 2014, vol. 32, 9 pgs.

Ranjan et al., "An All-In-One Convolutional Neural Network for Face Analysis", Center for Automation Research, UMIACS, University of Maryland, College Park, MD 20742, Nov. 3, 2016, 9 pgs.

First Office Action dated Aug. 16, 2021, in connection with Chinese Patent Application No. 20180127713.2, filed Feb. 8, 2018, 20 pgs (including translation).

Dai, Jifeng, et al.: "Istance-aware Semantic Segmentation via Multi-task Network Cascades"; CVPR; pp. 3150-3158, Dec. 31, 2016.

* cited by examiner

HIERARCHICAL LEARNING OF WEIGHTS OF A NEURAL NETWORK FOR PERFORMING MULTIPLE ANALYSES

CROSS-REFERENCE TO RELATED APPLICATIONS

This application claims the benefit of U.S. Provisional Application No. 62/456,368, filed Feb. 8, 2017, the disclosure of which is herein incorporated by reference in its entirety.

BACKGROUND OF THE INVENTION

The present invention relates generally to medical imaging analysis, and more particularly to a hierarchical approach for exploiting commonalities in different medical imaging analyses.

Medical imaging analysis involves extracting information from medical imaging data for performing medical tasks, such as landmark detection, anatomy detection, lesion detection, anatomy segmentation, segmentation and characterization, cross-modality image registration, image de-noising, etc. Machine learning methods have been widely used for the automation of medical imaging analysis. By learning relationships from a large database of annotated training imaging data, machine learning methods are able to extract representative features from medical imaging data and make meaningful predictions. Recently, neural networks (NNs), and in particular convolutional neural networks (CNNs), have been widely used in medical imaging analysis. A CNN is primarily characterized by its network architecture, which specifies how to stack layers of convolution pooling into one computational entity, and kernel coefficients associated with the convolution layers. Conventional CNNs are constructed (with their own network architecture) and learned (with their own kernel coefficients) to perform a specific medical imaging analysis associated with a specific modality, anatomy, and task.

Conventional CNNs developed for performing a specific medical imaging analysis do not take into account commonalities inherent among different medical imaging analyses. For example, such commonalities may include the imaging modality, target anatomical structure, and low-level features (e.g., Gabor-like features commonly found in the kernels belonging to the early CNN convolution layers).

BRIEF SUMMARY OF THE INVENTION

In accordance with one or more embodiments, systems and methods are provided for performing medical imaging analysis. Input medical imaging data is received for performing a particular one of a plurality of medical imaging analyses. An output that provides a result of the particular medical imaging analysis on the input medical imaging data is generated using a neural network trained to perform the plurality of medical imaging analyses. The neural network is trained by learning one or more weights associated with the particular medical imaging analysis using one or more weights associated with a different one of the plurality of medical imaging analyses. The generated output is outputted for performing the particular medical imaging analysis.

In accordance with one or more embodiments, each of the plurality of medical analyses is associated with a different modality, anatomy, and/or task. The task comprises at least one of detection, recognition, segmentation, and registration.

In accordance with one or more embodiments, the neural network is trained by learning a set of weights for each node of the neural network. The weights in the set of weights for each node have a hierarchical relationship such that a weight at a top level of the hierarchical relationship is associated with each of the plurality of medical imaging analyses and weights at a bottom level of the hierarchical relationship are each associated with a respective one of the plurality of medical imaging analyses.

In accordance with one or more embodiments, the set of weights for each node includes: a hypernet weight comprising the weight at the top level of the hierarchical relationship, one or more ultranet weights each associated with a modality and one or more ultranet weights each associated with an anatomy, one or more supernet weights each associated with a modality and an anatomy, and a plurality of target network weights comprising the weights at the bottom level of the hierarchical relationship.

In accordance with one or more embodiments, the set of weights for each node of the neural network are learned by cascading weights at a higher level of the hierarchical relationship to learn weights at a lower level of the hierarchical relationship associated with a same modality and/or anatomy. In another embodiment, the set of weights for each node of the neural network are learned by combining weights for a first node in the neural network that are associated with at least one of a same modality, anatomy, and task to form a combined weight; and learning weights for a second node in the neural network using the combined weight.

In accordance with one or more embodiments, the neural network is trained using datasets of training medical imaging data. Each of the datasets are associated with a respective one of the plurality of medical imaging analyses and used to train a target network representing a branch of the neural network for performing the respective one of the plurality of medical imaging analyses. The datasets of training medical imaging data include input training medical imaging data. Output training medical imaging data is generated corresponding to the input training medical imaging data using multi-task learning, the multi-task learning trained based on a relationship learned using an image as an input and an output These and other advantages of the invention will be apparent to those of ordinary skill in the art by reference to the following detailed description and the accompanying drawings.

DETAILED DESCRIPTION

The present invention generally relates to a hierarchical learning of weights of a neural network to exploit commonalities between different medical imaging analyses performed by the neural network. Embodiments of the present invention are described herein to give a visual understanding of methods for optimizing contrast imaging of a patient. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be described with respect to learning a neural network for medical imaging analysis of a patient, the present invention is not so limited. Embodiments of the present invention may be applied for performing any type of analysis on any subject using a neural network.

Figure 1:
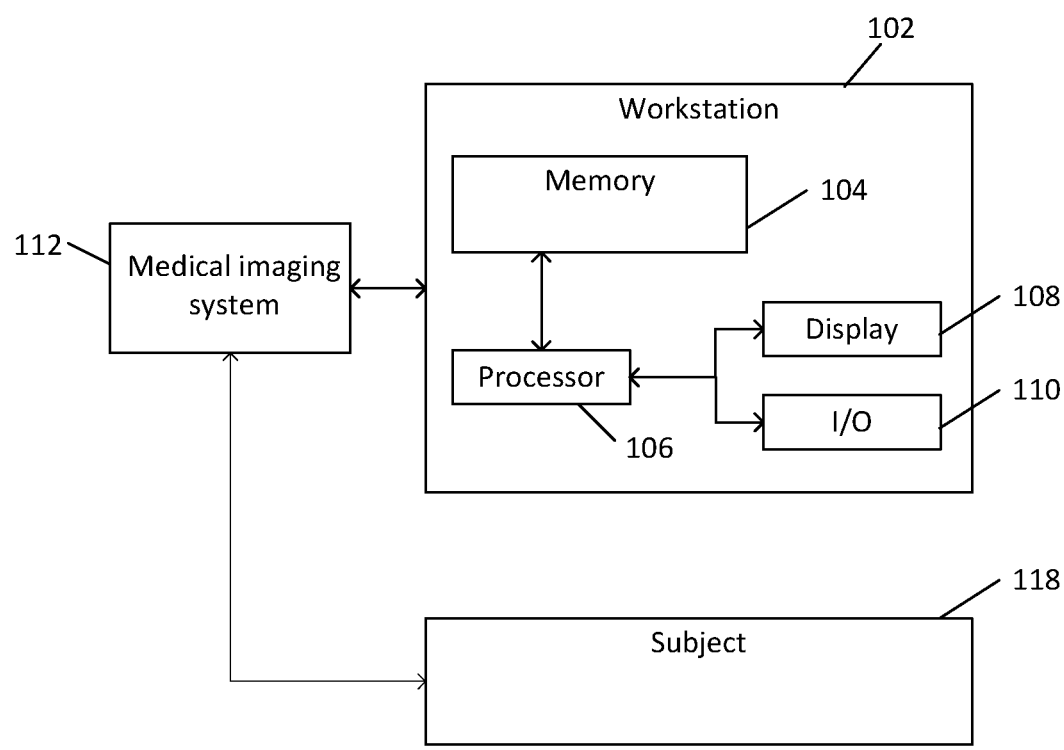
FIG. 1 shows an exemplary system for the analysis of medical imaging data, in accordance with one or more embodiments.

FIG. 1 shows a system 100 for the analysis of medical imaging data of a patient, in accordance with one or more embodiments. System 100 includes workstation 102, which may be used for assisting a user (e.g., a doctor, clinician, or any other medical professional) during a medical task, such as, e.g., detection, recognition, segmentation, and registration. Workstation 102 includes one or more processors 106 communicatively coupled to memory 104, display device 108, and input/output devices 110. Memory 104 may store computer program instructions (e.g., code) for performing operations that, when executed on processor 106, represent functionality of workstation 102. It should be understood that workstation 102 may also include additional elements not shown in FIG. 1, such as, e.g., a communications interface.

Workstation 102 may receive medical imaging data from medical imaging system 112 imaging a subject 118 (e.g., a patient) for assisting a clinician (or other user) for performing one or more medical imaging analyses. Medical imaging system 112 may be of any modality, such as, e.g., x-ray, magnetic resonance imaging (MRI), computed tomography (CT), ultrasound (US), single-photon emission computed tomography (SPECT), positron emission tomography (PET), or any other suitable modality or combination of modalities. In one embodiment, the medical imaging data is received directly from the medical imaging system 112 imaging subject 118. In another embodiment, the medical imaging data is received by loading previously stored imaging data of subject 118.

As discussed herein, medical imaging analysis refers to the analysis of medical imaging data of a particular modality for a target anatomy to perform one or more medical tasks. It should be understood that the embodiments described herein may relate to any type of medical imaging analysis, comprising any combination of modality, anatomy, and task. Illustrative examples of the one or more medical tasks include, e.g., detection, recognition, segmentation, or image registration. The modality of the medical imaging data may include, e.g., x-ray, MRI, CT, US, SPECT, PET, etc. The anatomy may include, e.g., liver, lung, kidney, etc. The medical imaging analysis may be performed using a neural network trained to predict outcomes associated with a modality, anatomy, and task from newly input medical imaging data of a patient.

Conventionally, a neural network is constructed with a particular network architecture and learned with its own kernel coefficients to predict outcomes to perform a particular medical imaging analysis (i.e., a specific modality, anatomy, and task). However, such conventional neural networks are unable to utilize the commonalties inherent among different medical imaging analyses.

Advantageously, embodiments discussed herein describe a single neural network configured to predict outcomes to perform a plurality of different medical imaging analyses, thereby exploiting commonalities amongst them. Such commonalities may arise from, e.g., the imaging modality, the target anatomical structure, and low level features (e.g., Gabor-like features).

Figure 2:
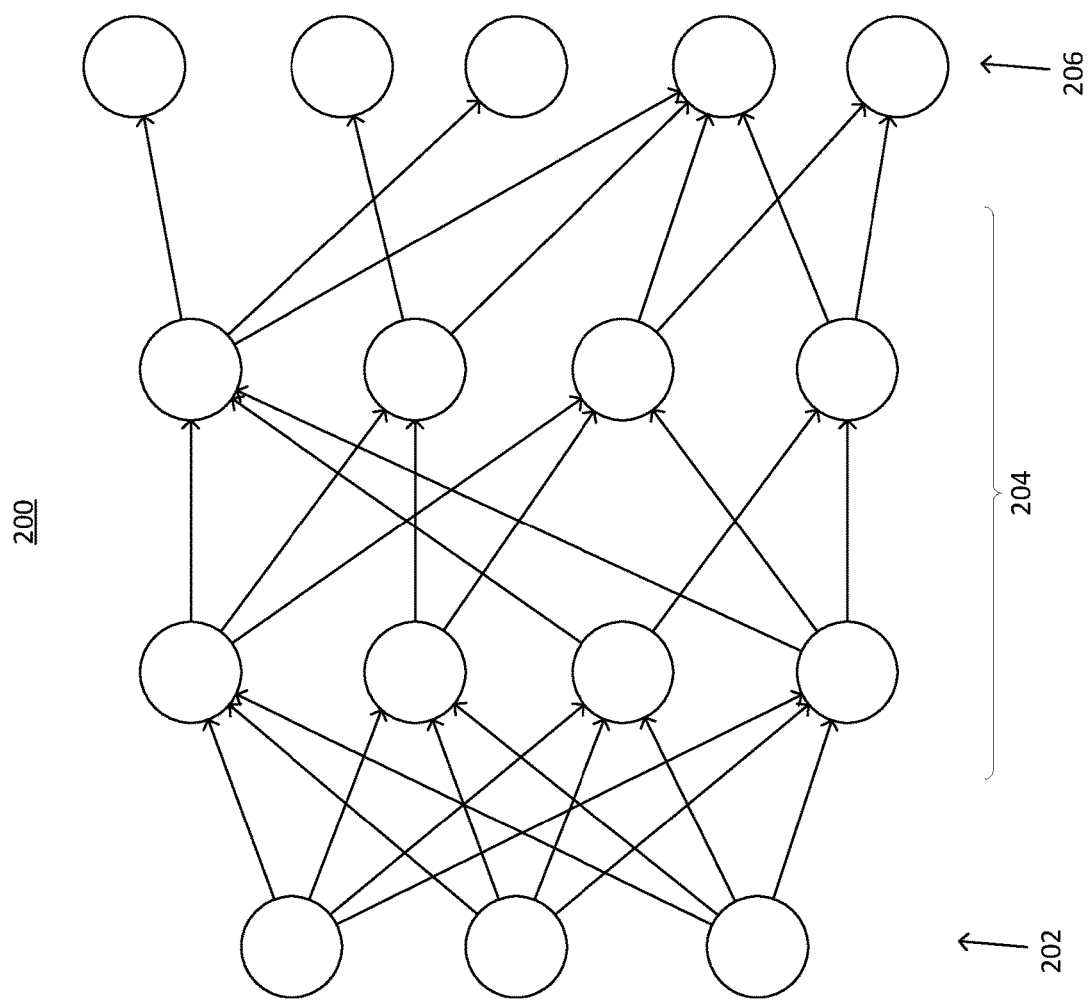
FIG. 2 shows an exemplary neural network, in accordance with one or more embodiments.

FIG. 2 shows an exemplary neural network 200, in accordance with one or more embodiments. Neural network 200 may be, e.g., a deep neural network (DNN), a convoluted neural network (CNN), or any other suitable type of neural network. Neural network 200 is trained to predict outcomes for a plurality of different medical imaging analyses, each associated with a particular modality, anatomy, and task. Neural network 200 includes an input layer 202, one or more hidden layers 204, and an output layer 206.

Medical imaging analysis is performed using newly input medical imaging data (e.g., one or more medical images) of a patient by applying neural network 200. Based on the medical imaging analysis being performed (i.e., based on the particular task, modality, and anatomy), a target network of neural network 200 is applied to perform the analysis. As discussed herein, the target network of neural network 200 refers to a path or branch representing a subset of nodes in neural network 200 associated with a particular modality, anatomy, and task for performing the particular medical imaging analysis.

Consider the following exemplary medical imaging analyses to be performed using neural network 200: liver detection from CT, liver segmentation from CT, lung detection from CT, liver segmentation from MR, and left kidney detection from MR. A new terminology is introduced: Net.Modality.Anatomy.Task, or Net. MAT, to denote a target network for performing medical imaging analysis associated with medical task T (where T=detection, recognition, segmentation, registration, etc.) related to target anatomical structure A (where A=liver, lung, left kidney, etc.) using image modality M (where M=CT, MR, PET, etc.). In the medical imaging analyses above, the target networks are denoted according to the defined terminology as Net.CT.Liver.Det, Net.CT.Liver.Seg, Net.CT.Lung.Det, Net.MR.Liver.Seg, Net.MR.LKidney.Det, respectively.

In one embodiment, neural network 200 is trained by learning a set or vector of weights associated with each node according to a hierarchical relationship. Accordingly, a weight at a top of the hierarchical relationship is associated with all medical imaging analyses that neural network 200 is trained to perform (i.e., all modalities, anatomies, and tasks) while weights at a bottom of the hierarchical relationship are associated with a respective one of the medical imaging analyses (i.e., a specific modality, anatomy, and task). Such a hierarchical relationship allows weights to be learned for all medical imaging analyses together, thereby leveraging training data associated with one medical imaging analysis to be used in performing another medical imaging analysis due to commonalities in, e.g., modality and/or anatomy between the medical imaging analyses.

In one embodiment, the hierarchical structure is denoted, from narrowest (bottom level) to broadest (top level), as: the target network Net.MAT, SuperNet, UltraNet, and HyperNet. It should be understood that the hierarchical structure described herein may be modified to provide deeper or shallower hierarchy (e.g., to remove or add new commonalities of interest), or be adopted for applications outside of medical imaging.

A SuperNet is denoted by the terminology SuperNet.Modality.Anatomy, or SuperNet.MA. A SuperNet constitutes the common portion among different tasks T for a same modality M and a same anatomy A. For example, the SuperNet.CT.Liver is shared by Net.CT.Liver.Det and Net.CT.Liver.Seg.

An UltraNet constitutes the common part among different SuperNets for a modality M or an anatomy A. In particular, the UltraNet.Modality, or UNet.M, constitutes the common part among different SuperNets related to the same modality M, regardless of anatomy A (or task T). The UltraNet.Anatomy, or UNet.A, constitutes the common part among different SuperNets related to a same anatomy A, regardless of modality M (or task T). For example, the UltraNet.CT is shared by SuperNet.CT.Liver and SuperNet.CT.Lung. In another example, the UltraNet.Liver is shared by SuperNet.CT.Liver and SuperNet.MR.Liver.

A HyperNet, or HNet, constitutes the common part among all UltraNets. The HyperNet may capture the low-level features, such as, e.g., Gabor-like features commonly found in kernels belonging to early CNN layers. There is only one HyperNet in the neural network for all medical imaging analyses (i.e., all modalities, all anatomies, and all tasks).

The target network, Net. MAT, represents a path or branch in neural network 200 associated with a particular modality, anatomy, and task for performing the particular medical imaging analysis. Mathematically, the target network Net.MAT for a medical procedure takes the form: Net(x; $W_H$, $W_M$, $W_A$, $W_{MA}W_{MAT}$) where $W_H$, is the kernel weights for the HNet, $W_M$ is the kernel weights for UNet.M, $W_A$ is the kernel weights for UNet.A, $W_{MA}$ is the kernel weights for SNet.MA, and $W_{MAT}$ is the kernel weights for the remaining part of Net.MAT.

Figure 3:
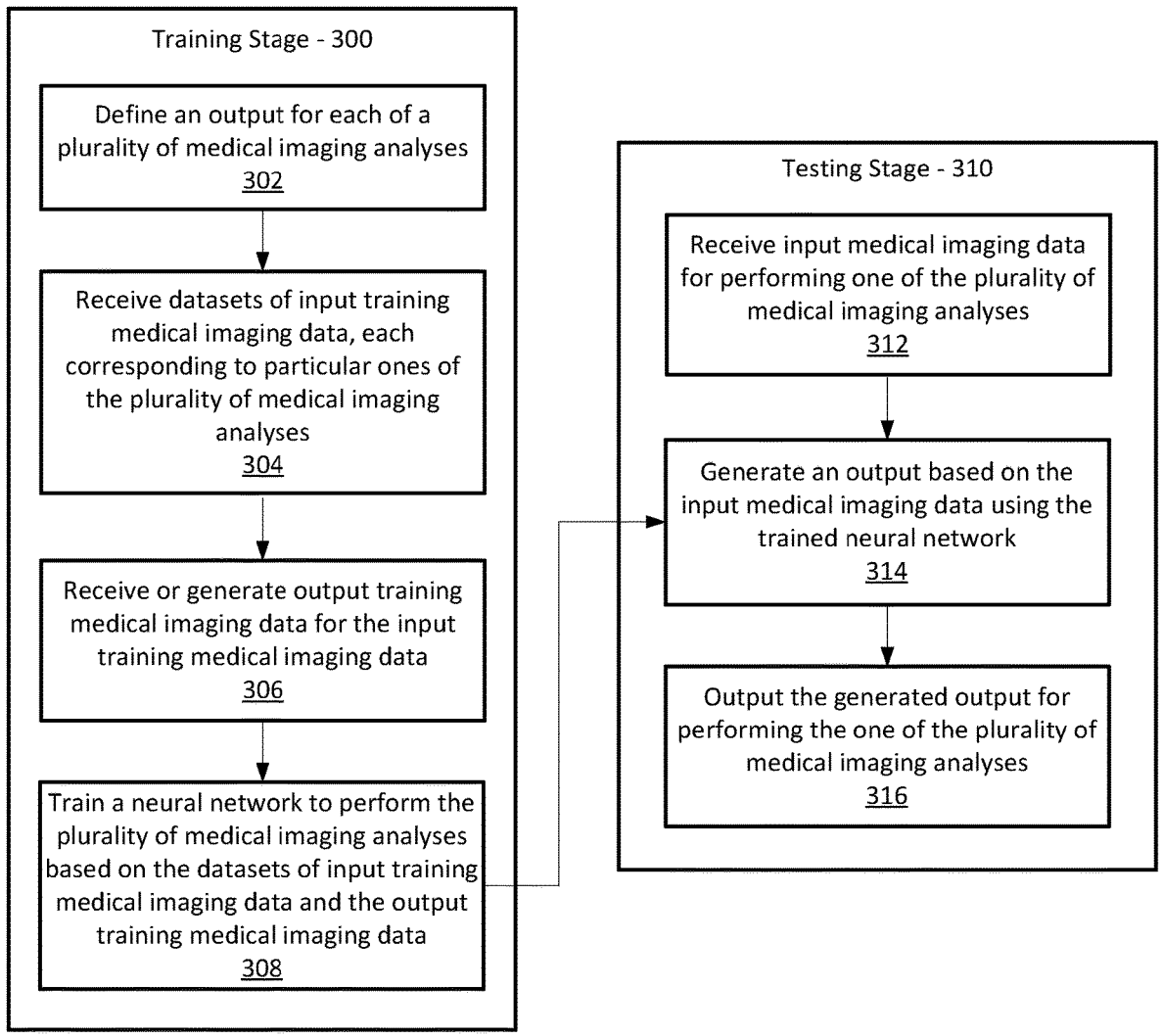
FIG. 3 shows a method for performing medical imaging analysis, in accordance with one or more embodiments.

FIG. 3 illustrates a method 300 for performing medical imaging analysis using a neural network, in accordance with one or more embodiments. In one embodiment, workstation 102 of FIG. 1 may execute computer program instructions on processor 106 for performing the steps of method 300.

The method of FIG. 3 includes a training stage 300 and a testing stage 310. The training stage 300, which includes steps 302-308, is performed offline to train a neural network (such as, e.g., neural network 200 of FIG. 2) for performing a plurality of medical imaging analyses. The testing stage 310, which includes steps 312-316, performs one of the plurality of medical imaging analyses on newly input medical imaging data using the trained neural network from training stage 300. Once the neural network is trained for performing the plurality of medical imaging analyses in training stage 300, the testing stage 310 can be repeated for each newly received input medical imaging data to perform a same one or different ones of the plurality of medical imaging analyses using the trained neural network.

During training stage 300, at step 302, an output is defined for each of a plurality of medical imaging analyses. The solutions or results for many medical imaging analyses are often not images. For example, anatomical landmark detection typically results in coordinates of a landmark location in the input image, while anatomy detection typically results in a pose (e.g., position, orientation, and scale) of a bounding box surrounding an anatomical object of interest in the input image.

In one embodiment, an output is defined for each of the plurality of medical imaging analyses that provides the result of that medical imaging analysis in the form of an image. In one possible implementation, the output for a particular medical imaging analysis can be automatically defined, for example by selecting a stored predetermined output format corresponding to the particular medical imaging analysis. In another possible implementation, user input can be received for selecting or defining an output format for a particular medical imaging analysis.

Any suitable format may be defined for each of the medical imaging analyses as is known in the art. In one embodiment, where the medical imaging analysis is landmark detection, the output is an image having a mask in which pixel locations of the landmark have a value of 1 and all other pixel locations have a value of 0. In another embodiment, where the medical imaging analysis is image registration, the output is an image of a deformation field. In another embodiment, where the medical imaging analysis is segmentation, the output is an image mask in which the pixels of the segmented object have a value 1 and others 0. In another embodiment, where the medical imaging analysis is recognition, the output is a multi-class label.

At step 304, datasets of input training medical imaging data are received. Each of the datasets are associated with one of a plurality of medical imaging analyses, and are therefore associated with a particular modality, anatomy, and task. It should be understood that at least some of the input training medical imaging data in the datasets may be associated with multiple datasets. The datasets of input training medical imaging data may be received by loading a number of previously stored input datasets of training medical imaging data from a database of medical images.

At step 306, output training medical imaging data is generated or received for the corresponding input training medical imaging data. In one embodiment, the output training medical imaging data may received with the datasets of input training medical imaging data (e.g., at a same time) at step 304. In another embodiment, the output training medical imaging data may be generated automatically or semi-automatically from the received input training medical imaging data based on, e.g., user input received via a user input device (e.g., mouse, touchscreen, etc.), existing algorithms (e.g., transfer learning or multitask learning), etc.

Figure 4:
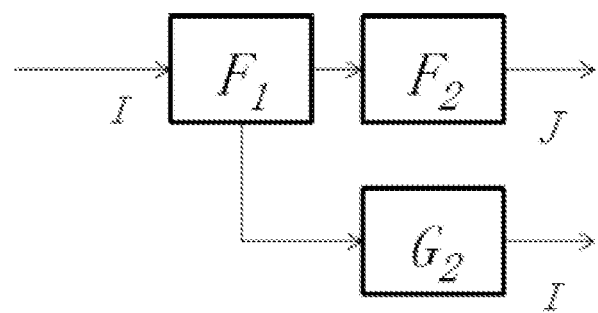
FIG. 4 shows a multi-task learning framework, in accordance with one or more embodiments.

In one embodiment, the output training medical imaging data is generated using multi-task learning. FIG. 4 shows a multi-task learning framework 400, in accordance with one or more embodiments. Multi-task learning aims to learn a network that produces multiple outputs, one for each medical imaging analysis, from an input image I. As shown in FIG. 4, common module F1 is shared for determining each of the outputs. Module F2 is an analysis-specific module (e.g., for landmark detection) to determine output image J. Multi-task learning framework 400 also include module G2, a self-reconstruction module for reconstructing input image I as output image I, such that input image I becomes the label. Accordingly, the self-reconstruction module G2 is leveraged to better learn common process F1, thereby improving the mapping between input image I and output image J.

For the self-reconstruction module G2, the amount of images available for training is almost unbounded. The overall multi-task learning network may learn from the whole universe of images from this domain. The features learned in this manner will have to be generic to this domain. This can greatly improve the generalization capability of this network, and thus the subpart of the network (i.e., analysis-specific module F2) will benefit.

Figure 5:
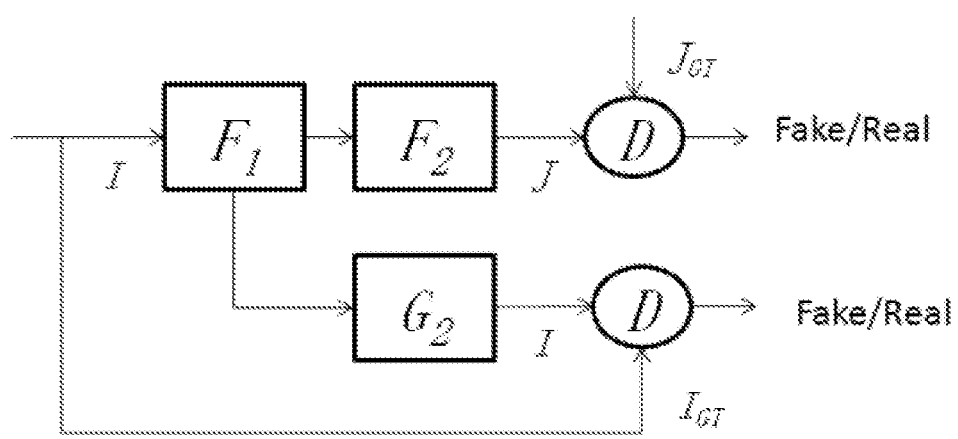
FIG. 5 shows a multi-task learning framework equipped with adversarial discriminators, in accordance with one or more embodiments.

In one embodiment, the multi-task learning framework 400 may be extended by equipping it with adversarial discriminators as shown in FIG. 5, in accordance with one or more embodiments. Multi-task learning framework 500 in FIG. 5 is equipped with adversarial discriminators D at each output for comparing output images J and/with ground truth output images $J_{GT}$ and $I_{GT}$ to determine if output images J and/are fake or real.

Returning back to step 306 of FIG. 3, the output medical imaging data (received or generated) may be annotated with ground truth measurements. The datasets of input training medical imaging data and the output medical imaging data may form i pairs of input and output training images $\{(x_{MAT}^i, y_{MAT}^i)\}$, where x is the input training medical image for performing a medical imaging analysis (i.e., for a particular modality, anatomy, and task) and y is the output training medical image desired when performing the medical imaging analysis. The output training medical imaging data is in a format as defined at step 302 according to its associated medical imaging analysis.

In accordance with the terminology defined herein, each dataset of training medical imaging data is denoted as DataSet.Modality.Anatomy.Task, or DataSet.MAT, to indicate the medical imaging analysis that the dataset is to be used for training the target network, Net.MAT. Accordingly, such annotation defines the nodes of the target network Net.MAT that the dataset is used to train.

At step 308, a neural network is trained to perform the plurality of medical imaging analyses based on the datasets of input training medical imaging data and the corresponding output training medical imaging data. The neural network is represented as a plurality of nodes each associated with a set or vector of weights. The weights in the set of weights correspond to the hierarchical structure of networks, such that each vector of weight includes a weight $W_H$ for the HNet, weight $W_M$ for UNet.M, weight $W_A$ for UNet.A, weight $W_{MA}$ for SNet.MA, and weight $W_{MAT}$ for the remaining part of Net.MAT. The hierarchical structure allows for weights at a top level of the hierarchy (i.e., $W_H$) to be used for learning weights further down the hierarchy (e.g., $W_M$, $W_A$, and $W_{MAT}$). Accordingly, datasets of training medical imaging data associated with one medical imaging analysis can be used for learning weights associated with a different medical imaging analysis.

Mathematically, the neural network is trained to perform the plurality of medical imaging analyses by minimizing the following combined loss function:

$$L = \Sigma_{MAT} \lambda_{MAT} \Sigma_i \text{LOSS}_{MAT}(\text{Net}(x_{MAT}^i; W_H, W_M, W_A, W_{MA}, W_{MAT}), y_{MAT}^i)$$ (Equation 1)

The loss function, $\text{LOSS}_{MAT}(\cdot)$ is specific to a particular medical imaging analysis. In one embodiment, $\text{LOSS}_{MAT}(\cdot)$ calculates an error or difference between predicted outcomes and the ground truth outcomes for the pairs $\{(x_{MAT}^i, y_{MAT}^i)\}$ of training images i associated with this particular medical imaging analysis. The coefficient $\lambda_{MAT}$ is a linear weight.

Advantageously, the hierarchical structuring of the networks, and their associated weights, allows datasets of training medical imaging data associated with one medical imaging analysis to be used for learning weights associated with a different medical imaging analysis based on the commonalities between the medical imaging analyses (e.g., modality, anatomy, or task). In other words, weights at associated with different hierarchical levels may be shared between other hierarchical levels in the hierarchical structure or other nodes or layers in the neural network. For example, medical imaging analyses for liver detection from CT and liver segmentation from CT may both be leveraged for learning weight $W_A$, which in turn may be leveraged for learning $W_{MA}$ and $W_{MAT}$ in some embodiments, even though the modalities and the tasks are different. The weights associated with networks in the hierarchical structure may be shared using any suitable approach. In one embodiment, the weights may be shared according to a cascade sharing mechanism, as further discussed below with reference to FIG. 6. In another embodiment, the weights may be shared according to an additive sharing mechanism, as further discussed below with reference to FIG. 7.

During testing stage 310, at step 312, input medical imaging data is received for performing one of the plurality of medical imaging analyses. The input medical imaging data may be one or more unlabeled medical image for performing the medical imaging analysis. Depending on the medical imaging analysis to be performed, the input medical imaging data may be a set of medical images. The input medical imaging data includes an indication of the medical imaging analysis to be performed, such as an annotation of the target network Net.MAT. The input medical imaging data may be received directly from a medical imaging system (e.g., medical imaging system 112 in FIG. 1) used to acquire the input medical imaging data. Alternatively, the input medical imaging data may be received by loading previously acquired medical imaging data from a storage or memory of a computer system, or receiving medical imaging data that has been transmitted from a remote computer system.

At step 314, an output that provides a result of the medical imaging analysis is generated from the input medical imaging data using the neural network trained at training stage 300. In particular, based on the weight $W_{MAT}$ learned for each node during training stage 300 for the target network Net.MAT, an output is found that minimizes Equation 1 for the received input medical imaging data. The output is in a format as defined at step 302 during training stage 300.

At step 316, the generated output, which provides the result of the medical imaging analysis for the input medical imaging data, is output. For example, the generated output can be output by displaying the generated output on a display device of a computer system. The generated output image can also be output by storing the generated output image on a memory or storage of a computer system, or by transmitting the generated output image to a remote computer system.

Advantageously, a set of weights for each node in the neural network are hierarchically learned, thereby allowing for weights associated with different medical imaging analyses (and thus different modalities, anatomies, and/or tasks) to be learned together. The present invention thereby reduces overfitting risk, improves generalization for all learned medical imaging analyses, and allows incremental training for an unseen application by using already learned network modules.

Figure 6:
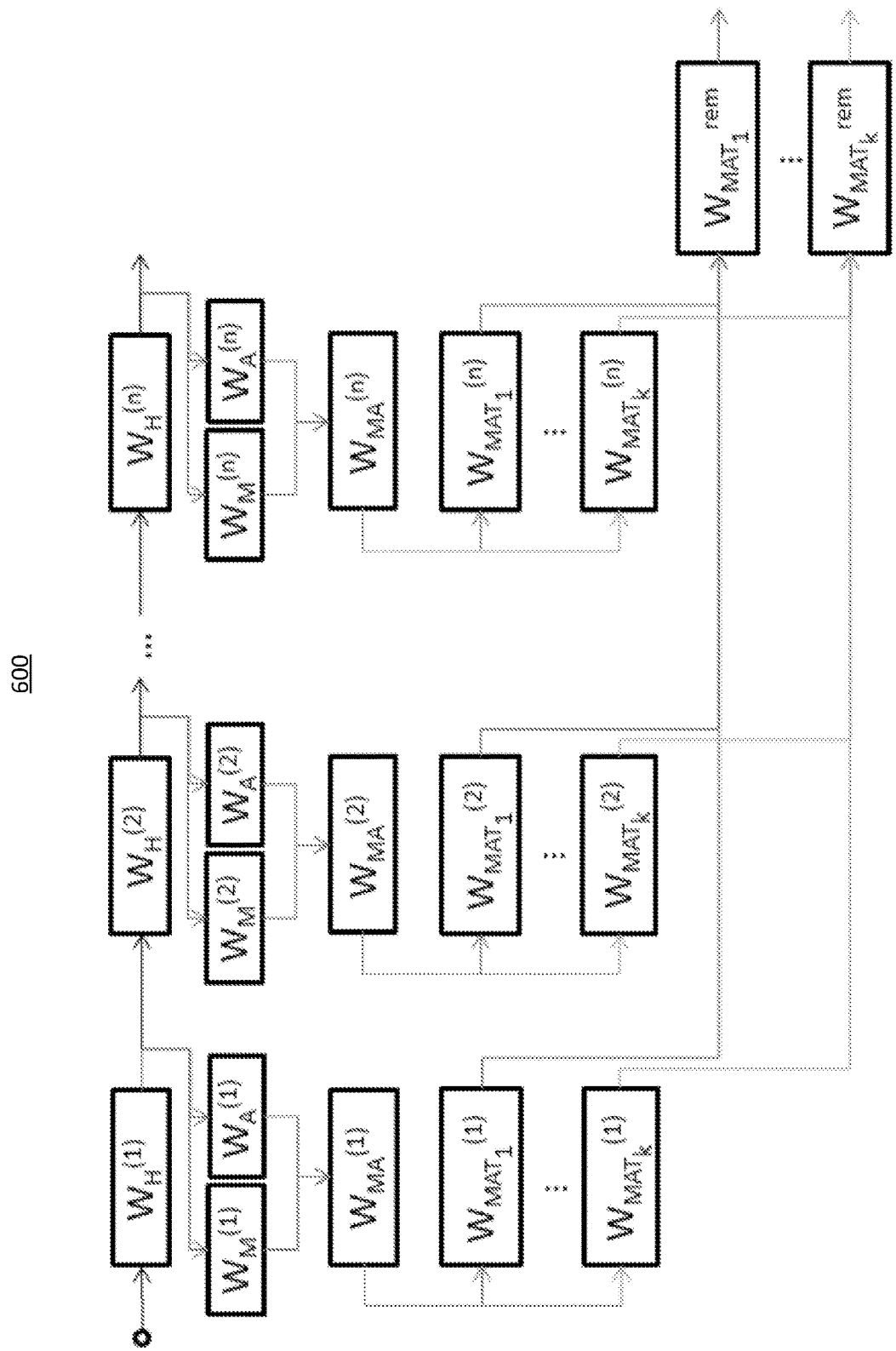
FIG. 6 shows a cascading mechanism for sharing weights, in accordance with one or more embodiments.

FIG. 6 shows an exemplary cascade sharing mechanism 600 for sharing weights according to the hierarchical structure described herein, in accordance with one or more embodiments. For layer 1 of the neural network, an HNet weight, $W_H(1)$, is first learned and cascaded down where it is leveraged to learn $W_H(2)$, the HNet weight for layer 2 (i.e., the next, subsequent layer). HNet weight, $W_H(1)$, is also cascaded down to learn UNet weights $W_M(1)$ and $W_A(1)$ for layer 1. One or more of UNet weights $W_M(1)$ and $W_A(1)$ are cascaded down to learn SNet weight $W_{MA}(1)$, which is cascaded down to learn target network Net.MAT weight $W_{MAT_1}(1), \ldots, W_{MAT_k}(1)$ for tasks 1 through k. Weight $W_{MAT_{rem}}(1)$ represents any remaining weights that do not fit into the hierarchical structure. Weights are similarly cascaded for the remaining n layers of the neural network.

Figure 7:
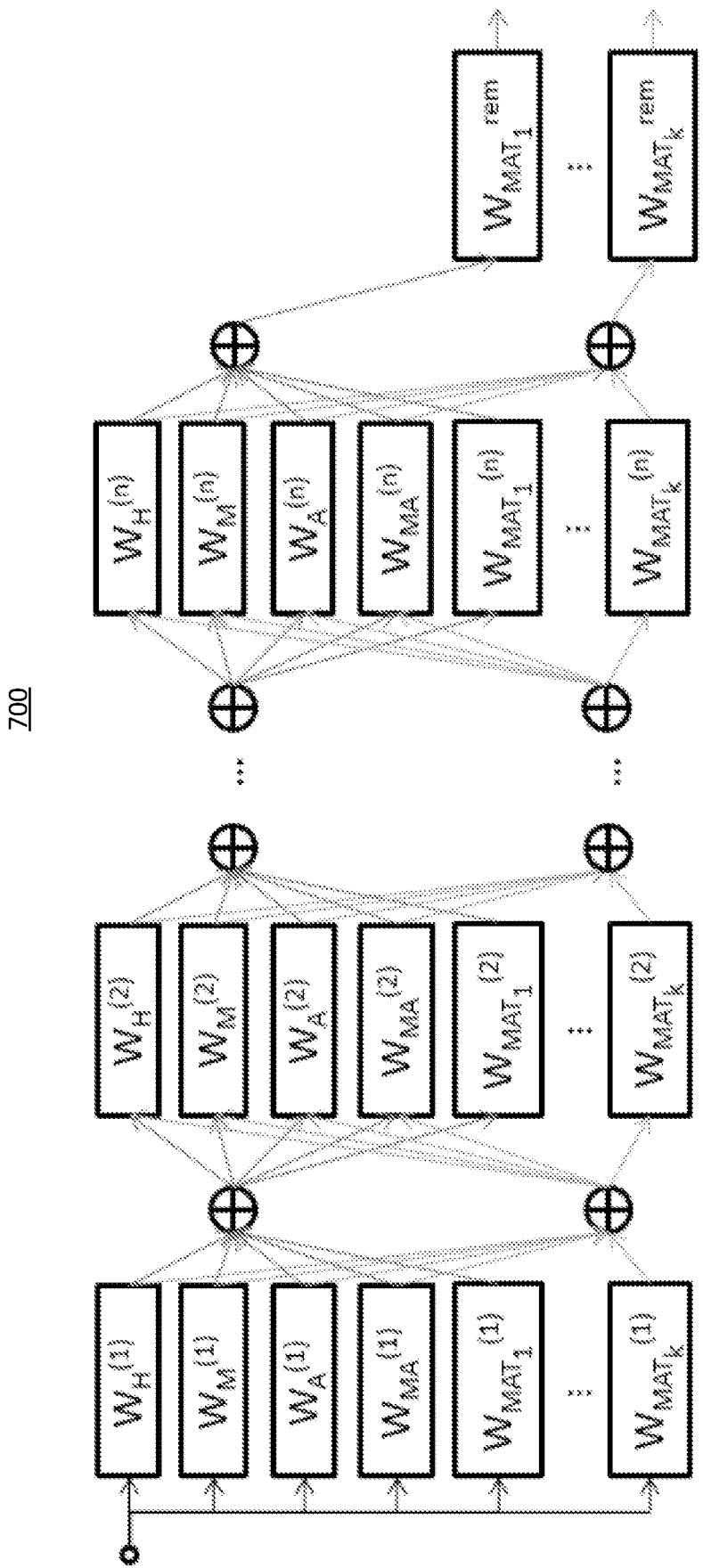
FIG. 7 shows an additive mechanism for sharing weights, in accordance with one or more embodiments.

FIG. 7 shows an exemplary additive sharing mechanism 700 for sharing weights associated with networks of the hierarchical structure, in accordance with one or more embodiments. For layer 1 of the neural network, a vector of weights $(W_H(1), W_M(1), W_A(1), W_{MA}(1), W_{MAT_k}(1))$ associated with task k are added to form a combined weight for each task 1, ..., k. The combined kernel weights for task k are shared with layer 2 and are used to learn each weight in the vector of weights for task k in layer 2 (i.e., the next, subsequent layer). For example, vector of weights for layer 1 $(W_H(1), W_M(1), W_A(1), W_{MA}(1), W_{MAT_{det}}(1))$ for the task detection are added to form a combined weight for the task detection, and the combined weight is used to learn vector of weights for layer 2 $(W_H(2), W_M(2), W_A(2), W_{MA}(2), W_{MAT_{det}}(2))$ for the task detection. Weights are similarly combined and shared for the remaining n layers of the neural network.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps of the methods and workflows described herein, including one or more of the steps of FIG. 3. Certain steps of the methods and workflows described herein, including one or more of the steps of FIG. 3, may be performed by a server or by another processor in a network-based cloud-computing system. Certain steps of the methods and workflows described herein, including one or more of the steps of FIG. 3, may be performed by a client computer in a network-based cloud computing system. The steps of the methods and workflows described herein, including one or more of the steps of FIG. 3, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps of FIG. 3, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 8:
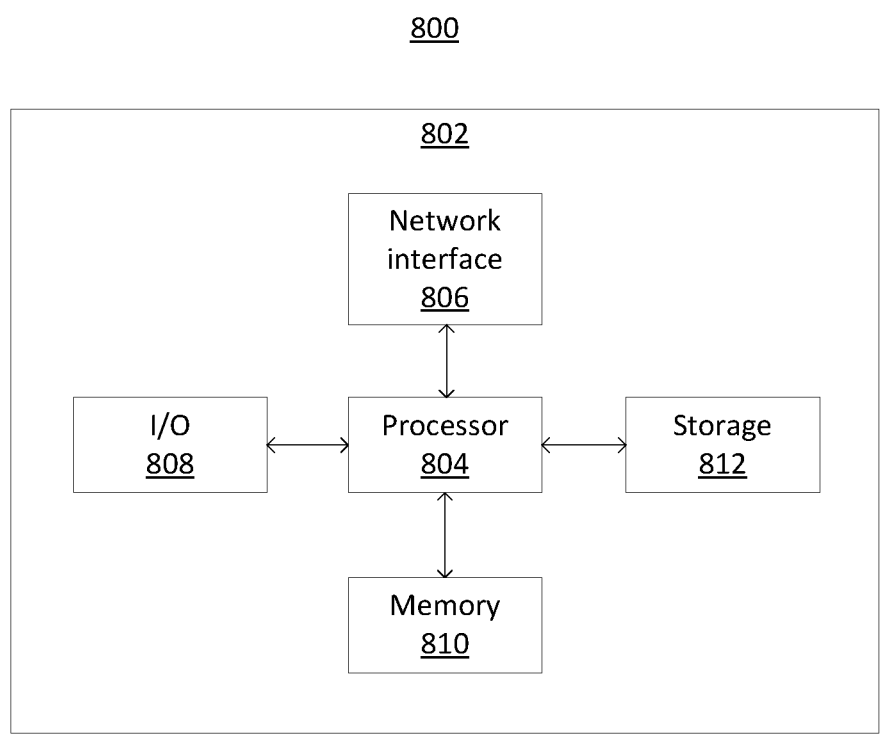
FIG. 8 shows a high-level block diagram of a computer, in accordance with one or more embodiments.

A high-level block diagram 800 of an example computer that may be used to implement systems, apparatus, and methods described herein is depicted in FIG. 8. Computer 802 includes a processor 804 operatively coupled to a data storage device 812 and a memory 810. Processor 804 controls the overall operation of computer 802 by executing computer program instructions that define such operations. The computer program instructions may be stored in data storage device 812, or other computer readable medium, and loaded into memory 810 when execution of the computer program instructions is desired. Thus, the method and workflow steps of FIG. 3 can be defined by the computer program instructions stored in memory 810 and/or data storage device 812 and controlled by processor 804 executing the computer program instructions. For example, the computer program instructions can be implemented as computer executable code programmed by one skilled in the art to perform the method and workflow steps of FIG. 3. Accordingly, by executing the computer program instructions, the processor 804 executes the method and workflow steps of FIG. 3. Computer 804 may also include one or more network interfaces 806 for communicating with other devices via a network. Computer 802 may also include one or more input/output devices 808 that enable user interaction with computer 802 (e.g., display, keyboard, mouse, speakers, buttons, etc.).

Processor 804 may include both general and special purpose microprocessors, and may be the sole processor or one of multiple processors of computer 802. Processor 804 may include one or more central processing units (CPUs), for example. Processor 804, data storage device 812, and/or memory 810 may include, be supplemented by, or incorporated in, one or more application-specific integrated circuits (ASICs) and/or one or more field programmable gate arrays (FPGAs).

Data storage device 812 and memory 810 each include a tangible non-transitory computer readable storage medium. Data storage device 812, and memory 810, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 808 may include peripherals, such as a printer, scanner, display screen, etc. For example, input/output devices 808 may include a display device such as a cathode ray tube (CRT) or liquid crystal display (LCD) monitor for displaying information to the user, a keyboard, and a pointing device such as a mouse or a trackball by which the user can provide input to computer 802.

Any or all of the systems and apparatus discussed herein, including elements of workstation 102 of FIG. 1, may be implemented using one or more computers such as computer 802.

One skilled in the art will recognize that an implementation of an actual computer or computer system may have other structures and may contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for performing medical imaging analysis, comprising:
    training a neural network by learning a set of weights for each node of the neural network, the weights in the set of weights for each node having a hierarchical relationship such that a weight at a top level of the hierarchical relationship is associated with each of a plurality of medical imaging analyses and weights at a bottom level of the hierarchical relationship are each associated with a respective one of the plurality of medical imaging analyses, wherein the set of weights for each node comprises:
        a hypernet weight comprising the weight at the top level of the hierarchical relationship;
        one or more ultranet weights each associated with a modality and one or more ultranet weights each associated with an anatomy;
        one or more supernet weights each associated with a modality and an anatomy; and
        a plurality of target network weights comprising the weights at the bottom level of the hierarchical relationship;
    receiving input medical imaging data for performing a particular one of the plurality of medical imaging analyses;
    generating an output that provides a result of the particular medical imaging analysis on the input medical imaging data using the neural network trained to perform the plurality of medical imaging analyses, wherein the neural network is trained by learning one or more weights associated with the particular medical imaging analysis using one or more weights associated with a different one of the plurality of medical imaging analyses; and
    outputting the generated output for performing the particular medical imaging analysis.

2. The method of claim 1, wherein each of the plurality of medical imaging analyses are associated with at least one of a different modality, anatomy, and task.

3. The method of claim 2, wherein the task comprises at least one of detection, recognition, segmentation, and registration.

4. The method of claim 1, wherein learning a set of weights for each node of the neural network comprises:
    cascading weights at a higher level of the hierarchical relationship to learn weights at a lower level of the hierarchical relationship associated with a same modality and/or anatomy.

5. The method of claim 1, wherein learning a set of weights for each node of the neural network comprises:
    combining weights for a first node in the neural network that are associated with at least one of a same modality, anatomy, and task to form a combined weight; and
    learning weights for a second node in the neural network using the combined weight.

6. The method of claim 1, wherein training a neural network comprises:
    training the neural network using datasets of training medical imaging data, each of the datasets being associated with a respective one of the plurality of medical imaging analyses and used to train a target network representing a branch of the neural network for performing the respective one of the plurality of medical imaging analyses.

7. The method of claim 6, wherein the datasets of training medical imaging data include input training medical imaging data, the method further comprising:
    generating output training medical imaging data corresponding to the input training medical imaging data using multi-task learning, the multi-task learning trained based on a relationship learned using an image as an input and an output.

8. An apparatus for performing medical imaging analysis, comprising:
    means for training a neural network by learning a set of weights for each node of the neural network, the weights in the set of weights for each node having a hierarchical relationship such that a weight at a top level of the hierarchical relationship is associated with each of a plurality of medical imaging analyses and weights at a bottom level of the hierarchical relationship are each associated with a respective one of the plurality of medical imaging analyses, wherein the set of weights for each node comprises:
        a hypernet weight comprising the weight at the top level of the hierarchical relationship;
        one or more ultranet weights each associated with a modality and one or more ultranet weights each associated with an anatomy;
        one or more supernet weights each associated with a modality and an anatomy; and
        a plurality of target network weights comprising the weights at the bottom level of the hierarchical relationship;
    means for receiving input medical imaging data for performing a particular one of the plurality of medical imaging analyses;

means for generating an output that provides a result of the particular medical imaging analysis on the input medical imaging data using the neural network trained to perform the plurality of medical imaging analyses, wherein the neural network is trained by learning one or more weights associated with the particular medical imaging analysis using one or more weights associated with a different one of the plurality of medical imaging analyses; and means for outputting the generated output for performing the particular medical imaging analysis.

9. The apparatus of claim 8, wherein each of the plurality of medical imaging analyses are associated with at least one of a different modality, anatomy, and task.

10. The apparatus of claim 9, wherein the task comprises at least one of detection, recognition, segmentation, and registration.

11. A non-transitory computer readable medium storing computer program instructions for performing medical imaging analysis, the computer program instructions when executed by a processor cause the processor to perform operations comprising:

training a neural network by learning a set of weights for each node of the neural network, the weights in the set of weights for each node having a hierarchical relationship such that a weight at a top level of the hierarchical relationship is associated with each of a plurality of medical imaging analyses and weights at a bottom level of the hierarchical relationship are each associated with a respective one of the plurality of medical imaging analyses, wherein the set of weights for each node comprises:

a hypernet weight comprising the weight at the top level of the hierarchical relationship;

one or more ultranet weights each associated with a modality and one or more ultranet weights each associated with an anatomy;

one or more supernet weights each associated with a modality and an anatomy; and a plurality of target network weights comprising the weights at the bottom level of the hierarchical relationship;

receiving input medical imaging data for performing a particular one of the plurality of medical imaging analyses;

generating an output that provides a result of the particular medical imaging analysis on the input medical imaging data using the neural network trained to perform the plurality of medical imaging analyses, wherein the neural network is trained by learning one or more weights associated with the particular medical imaging analysis using one or more weights associated with a different one of the plurality of medical imaging analyses; and outputting the generated output for performing the particular medical imaging analysis.

12. The non-transitory computer readable medium of claim 11, wherein learning a set of weights for each node of the neural network comprises:

cascading weights at a higher level of the hierarchical relationship to learn weights at a lower level of the hierarchical relationship associated with a same modality and/or anatomy.

13. The non-transitory computer readable medium of claim 11, wherein learning a set of weights for each node of the neural network comprises:

combining weights for a first node in the neural network that are associated with at least one of a same modality, anatomy, and task to form a combined weight; and learning weights for a second node in the neural network using the combined weight.

14. The non-transitory computer readable medium of claim 11, wherein training a neural network comprises:

training the neural network using datasets of training medical imaging data, each of the datasets being associated with a respective one of the plurality of medical imaging analyses and used to train a target network representing a branch of the neural network for performing the respective one of the plurality of medical imaging analyses.

15. The non-transitory computer readable medium of claim 14, wherein the datasets of training medical imaging data include input training medical imaging data, the operations further comprising:

generating output training medical imaging data corresponding to the input training medical imaging data using multi-task learning, the multi-task learning trained based on a relationship learned using an image as an input and an output.

* * * * *